United States Patent
Thakur et al.

(10) Patent No.: US 10,947,172 B2
(45) Date of Patent: Mar. 16, 2021

(54) HIGHLY ACTIVE CATALYST FOR DEHYDROGENATION OF ALKANES AND METHOD OF PREPARATION THEREOF

(71) Applicant: Indian Oil Corporation Limited, Mumbai (IN)

(72) Inventors: Ram Mohan Thakur, Haryana (IN); Hima Bindu Doosa, Haryana (IN); Kamlesh Gupta, Haryana (IN); Debasis Bhattacharyya, Haryana (IN); Sanjiv Kumar Mazumdar, Haryana (IN); Sankara Sri Venkata Ramakumar, Haryana (IN)

(73) Assignee: Indian Oil Corporation Limited, Mumbai (IN)

(*) Notice: Subject to any disclaimer, the term of this patent is extended or adjusted under 35 U.S.C. 154(b) by 0 days.

(21) Appl. No.: 16/657,726

(22) Filed: Oct. 18, 2019

(65) Prior Publication Data

US 2020/0199043 A1 Jun. 25, 2020

(30) Foreign Application Priority Data

Nov. 21, 2018 (IN) .............................. 201821043912

(51) Int. Cl.
*B01J 37/00* (2006.01)
*C07C 5/333* (2006.01)
(Continued)

(52) U.S. Cl.
CPC .............. *C07C 5/3335* (2013.01); *B01J 21/04* (2013.01); *B01J 21/18* (2013.01); *B01J 23/26* (2013.01);
(Continued)

(58) Field of Classification Search
CPC ..... C07C 5/333; C07C 5/3332; C07C 5/3335; C07C 5/3337; C07C 5/42; C07C 5/48; C07C 2521/04; C07C 2521/06; C07C 2523/02; C07C 2523/04; C07C 2523/26; C07C 11/02; B01J 35/023; B01J 35/1019; B01J 35/1038; B01J 37/0036; B01J 37/0063; B01J 37/009; B01J 37/0201; B01J 37/0236; B01J 37/036; B01J 37/04; B01J 37/08; B01J 37/082; B01J 37/18; B01J 21/04; B01J 21/18; B01J 23/24;
(Continued)

(56) References Cited

U.S. PATENT DOCUMENTS

| 4,727,052 | A | * | 2/1988 | Wan | ..................... B01J 37/0242 |
|---|---|---|---|---|---|
| | | | | | 502/327 |
| 8,680,357 | B1 | * | 3/2014 | Rokicki | ................ C07C 5/3332 |
| | | | | | 585/663 |

(Continued)

*Primary Examiner* — Brian A McCaig
(74) *Attorney, Agent, or Firm* — Blank Rome LLP

(57) ABSTRACT

The invention discloses a novel method for preparation of highly active and selective dehydrogenation catalyst, comprising of metal oxide of group VIB elements of periodic table, and at least one metal oxide from group IA and/or group VIII, supported on alumina or silica or mixture thereof, wherein the accessibility to active sites and dispersion of metal oxides is enhanced by the addition of carbonaceous material such as coke derived from coal or petroleum coke or any other form of carbon, during catalyst preparation and its combustion thereof during calcination.

7 Claims, 1 Drawing Sheet

(51) Int. Cl.

| | | |
|---|---|---|
| *B01J 37/08* | (2006.01) | |
| *B01J 37/18* | (2006.01) | |
| *B01J 21/04* | (2006.01) | |
| *B01J 37/02* | (2006.01) | |
| *B01J 23/26* | (2006.01) | |
| *B01J 21/18* | (2006.01) | |
| *B01J 35/10* | (2006.01) | |

(52) U.S. Cl.
CPC ....... *B01J 35/1019* (2013.01); *B01J 35/1038* (2013.01); *B01J 37/009* (2013.01); *B01J 37/0063* (2013.01); *B01J 37/0201* (2013.01); *B01J 37/0236* (2013.01); *B01J 37/08* (2013.01); *B01J 37/18* (2013.01); *C07C 5/3337* (2013.01); *C07C 2521/04* (2013.01); *C07C 2523/02* (2013.01); *C07C 2523/26* (2013.01)

(58) Field of Classification Search
CPC .... B01J 23/26; B01J 23/6522; B01J 23/6525; B01J 23/6527
See application file for complete search history.

(56) References Cited

U.S. PATENT DOCUMENTS

| | | |
|---|---|---|
| 2003/0163012 A1 | 8/2003 | Heineke et al. |
| 2007/0111886 A1* | 5/2007 | Serafin ................. B01J 37/0201 502/348 |
| 2009/0182186 A1 | 7/2009 | Benderly et al. |

\* cited by examiner

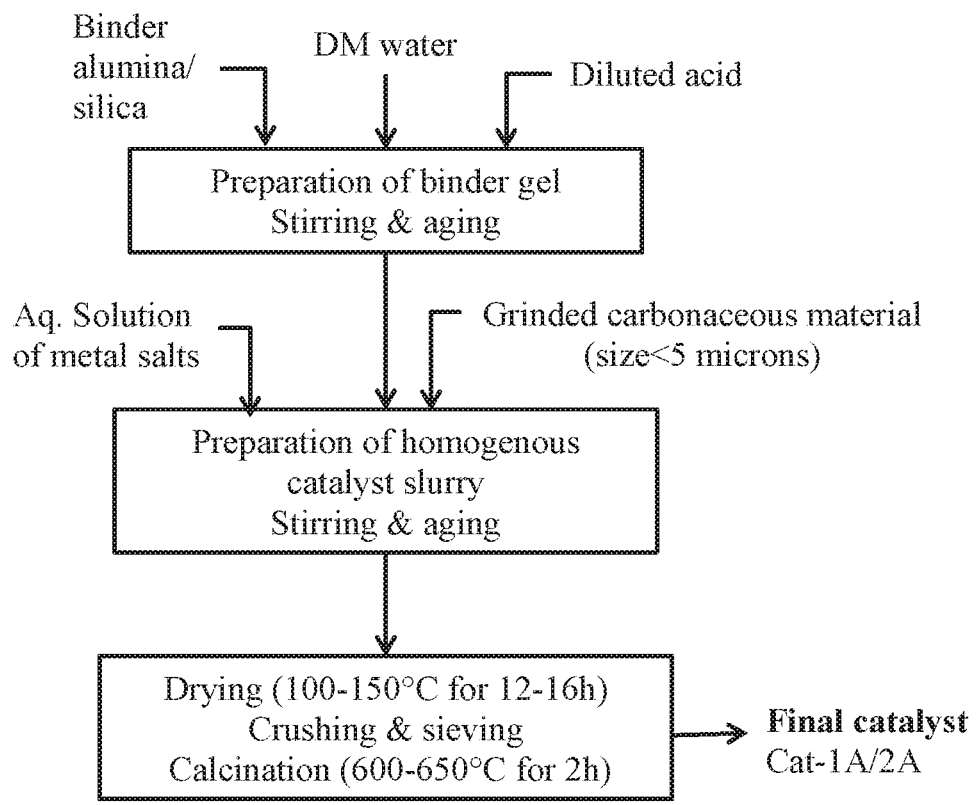

HIGHLY ACTIVE CATALYST FOR DEHYDROGENATION OF ALKANES AND METHOD OF PREPARATION THEREOF

RELATED APPLICATION

This application claims the benefit of Indian Application No. 201821043912, filed on Nov. 21, 2018. The entire content of this application is incorporated herein by reference.

FIELD OF THE INVENTION

The present invention relates to a method for the preparation of a catalyst for dehydrogenation of alkanes to alkenes, utilizing carbonaceous materials, such as, petroleum coke, activated charcoal, etc. and using metal oxides as active components. The present invention further relates to a catalyst comprising metal oxides as active components and prepared by utilizing carbonaceous materials.

BACKGROUND OF THE INVENTION

Propylene is an important precursor in petrochemical industry used for the production of polypropylene and other chemicals such as, propylene oxide, acrylonitrile, acrylic acid, cumene, etc. Conventional sources of propylene are steam cracking and fluid catalytic cracking (FCC). With the increasing global demand for propylene, on-purpose propylene production technologies such as, Propane dehydrogenation process became significant.

For propane dehydrogenation process, alumina supported noble metal catalysts, such as, $Pt/Al_2O_3$, $Pt$—$Sn/Al_2O_3$ or alumina supported CrOx based catalysts are extensively used. US patent US 2003/0163012 A1 discloses a catalyst composition for the preparation of unsaturated hydrocarbons from corresponding paraffinic hydrocarbons, comprising of an oxide of transition metal of group IVB of the periodic table, e.g. $TiO_2$ or $ZrO_2$, and possibly at least one element selected from the transition group VIII, e.g. Pd or Pt. and/or an element of transition group VI, e.g. Cr or Mo, and/or Rh, and/or Sn, and possibly a compound of an alkali metal or alkaline earth metal, and a compound of main group III or transition group III or Zn.

US patent US 2009/0182186 A1 describes a process for the conversion of propane to propylene wherein a silica chromium catalyst is contacted with propane and $CO_2$. Further, the catalyst includes a promoter component (optionally) from V, Ag, Ce, Mo, Nz, Zr oxides and combination thereof.

For higher performance of the catalyst, better dispersion of active metal sites and easy accessibility to the active sites is necessary.

SUMMARY OF THE INVENTION

Accordingly, the present invention provides a method of preparation of a catalyst for the production of light olefins by dehydrogenation of the respective paraffins. The activity and selectivity of the catalyst are enhanced by the addition of carbonaceous materials during the catalyst preparation.

The present invention relates to a method of preparation of a catalyst utilizing carbonaceous materials, such as, petroleum coke, activated charcoal, etc. The addition of carbonaceous material such as petroleum coke, activated charcoal etc. during the catalyst preparation results in an enhancement in the accessibility of the active sites due to the formation of extra pores and/or channels by the combustion of the added carbonaceous material during calcination.

In one of the features of the present invention, the process for preparation of a catalyst for dehydrogenation of alkane comprises of the following steps:
(a) wet grinding of carbonaceous material to obtain a grinded paste of the carbonaceous material;
(b) adding alumina to an organic acid solution under stirring for 15-20 minutes to form a gel and ageing the gel for 15-20 minutes;
(c) preparing aqueous solution of salts of metals of Groups IA, and/or VIB and/or VIII using suitable metal salts;
(d) adding the grinded paste of the carbonaceous material obtained in step (a) and the aqueous solution of salts of metals obtained in step (c) to the alumina gel obtained in step (b) to obtain a homogeneous catalyst slurry;
(e) drying the catalyst slurry obtained in step (d) at 100-150° C. for 12-16 hours to get a dry cake of catalyst;
(f) crushing the dried cake of catalyst obtained in step (e) and sieving to obtain catalyst particles of 0.5-1.0 mm for fixed bed operation and particles of 20-200μ for fluidized bed operation;
(g) calcining the catalyst particles obtained in step (f) at 600-650° C. at a ramp rate of 2.0° C./min for 2 hours in presence of air; and
(h) reducing the catalyst obtained in step (g) in a fixed bed/fixed-fluidized bed reactor using hydrogen gas, at 600-800° C. at a controlled flow rate to obtain final catalyst.

In another feature of the present invention, the carbonaceous material used in the process of preparation of the catalyst is any known carbonaceous material. In a preferred feature, the carbonaceous material is selected from a group comprising of petroleum coke, activated charcoal, graphite powder, or a combination thereof.

In another feature, the present invention further relates to a catalyst comprising metal oxides as active components and prepared utilizing carbonaceous materials based on the process of the present invention. The catalyst for dehydrogenation of alkanes comprises:
(i) 0.01-20 wt % of a metal of Group VIB;
(ii) 0.001-5 wt % of metals of Group IA and/or Group VIII; and
(v) support material,
wherein the wt % being based on the total weight of the catalyst.

In yet another feature of the present invention, the support material is selected from alumina, silica or mixture thereof.

The present invention further relates to the application of the catalyst for conversion of light paraffins to light olefins in the range of 35-60 wt % with selectivity for respective light olefin, in the range of 40-90 wt %.

OBJECTIVES OF THE INVENTION

The primary objective of the present invention is to provide a novel process for the preparation of porous and highly dispersed metal oxide catalyst utilizing carbonaceous materials such as, petroleum coke, activated charcoal, etc. on a suitable support such as alumina or silica or mixture thereof.

Another objective of the invention is to provide a catalyst for dehydrogenation of alkanes to alkenes with higher activity and selectivity for light olefins.

BRIEF DESCRIPTION OF DRAWING

FIG. 1: Schematic representation of the disclosed process for preparation of a catalyst for dehydrogenation of alkanes

DETAILED DESCRIPTION OF THE INVENTION

The present invention relates to a method for preparation of a catalyst for dehydrogenation of alkanes to alkenes, utilizing carbonaceous material, such as, petroleum coke, activated charcoal, etc. and non-precious metals or metal oxides as active components. The accessibility to the active sites is enhanced due to the formation of channels by the combustion of the added carbonaceous material during calcination.

According to the main feature, the present invention describes a method for preparation of a catalyst for dehydrogenation of alkanes to alkenes, utilizing carbonaceous material such as petroleum coke. Additional pores and/or channels are generated in the catalyst for providing accessibility of reactant molecules to active sites, and metal oxides are uniformly dispersed by the addition of carbonaceous materials, such as, petroleum coke, activated charcoal during the catalyst preparation and subsequently its combustion thereof during calcination. The process for preparation of the catalyst comprises of the following steps:
(a) wet grinding of carbonaceous material to obtain a grinded paste of the carbonaceous material;
(b) adding alumina to an organic acid solution under stirring for 15-20 minutes to form a gel and ageing the gel for 15-20 minutes;
(c) preparing aqueous solution of salts of metals of Groups IA, and/or VIB and/or VIII using suitable metal salts;
(d) adding the grinded paste of the carbonaceous material obtained in step (a) and the aqueous solution of salts of metals obtained in step (c) to the alumina gel obtained in step (b) to obtain a homogeneous catalyst slurry;
(e) drying the catalyst slurry obtained in step (d) at 100-150° C. for 12-16 hours to get a dry cake of catalyst;
(f) crushing the dried cake of catalyst obtained in step (e) and sieving to obtain catalyst particles of 0.5-1.0 mm for fixed bed operation and particles of 20-200μ for fluidized bed operation;
(g) calcining the catalyst particles obtained in step (f) at 600-650° C. at a ramp rate of 2.0° C./min for 2 hours in presence of air; and
(h) reducing the catalyst obtained in step (g) in a fixed bed/fixed-fluidized bed reactor using hydrogen gas, at 600-800° C. at a controlled flow rate to obtain final catalyst.

In another feature of the present invention, the carbonaceous material used in the process of preparation of the catalyst is any known carbonaceous material. In a preferred feature, the carbonaceous material is selected from a group comprising of petroleum coke, activated charcoal, graphite powder, or a combination thereof.

In a preferred feature of the present invention, the metal of Group VIB is selected from the group consisting of chromium, molybdenum, and tungsten.

In another preferred feature of the present invention, the metal of Group VIII is selected from the group consisting of iron, cobalt, rhodium, iridium, nickel, palladium, and platinum and the metal of Group IA is selected from the group consisting of lithium, sodium, potassium, rubidium, and cesium.

In a feature of the present invention, the carbonaceous material used in step (a) of the process of preparation of the catalyst, is wet grinded to a particle size ranging from 1 to 5μ.

In a preferred feature of the present invention, the organic acid used for the preparation of alumina gel is formic acid.

In yet another feature of the present invention, the formic acid solution is prepared by adding 10% by volume of formic acid in distilled water.

In a further feature, the present invention discloses a catalyst for dehydrogenation of alkanes, wherein the catalyst comprises of metal oxides of transition group as active ingredients, particularly from groups VIB, and/or VIII and possibly one metal from alkali group, supported on alumina or silica or mixture thereof. The catalyst is prepared utilizing carbonaceous materials based on the process of the present invention. The catalyst for dehydrogenation of alkanes comprises:
(i) 0.01-20 wt % of a metal of Group VIB;
(ii) 0.001-5 wt % of metals of Group IA and/or Group VIII; and
(iii) support material,
wherein the wt % being based on the total weight of the catalyst.

In a feature of the present invention, the support material is selected from alumina or silica or mixture thereof.

In a preferred feature, the content of the metal of group VIB in the catalyst ranges from 0.1-12 wt %.

In a preferred feature, the content of the metals of group VIII and group IA in the catalyst ranges from 0.005 to 2.5 wt %.

In yet another feature, the present invention discloses the step of contacting the prepared catalyst with feed stream containing light paraffins or mixture of paraffins and diluents, wherein the diluents could be $CO_2$, $N_2$, steam, inert gas, flue gas or combination thereof, is carried out at 500-700° C., at pressure 0.01 to 10 bar and GHSV (gas hourly space velocity) of 500-3000 $h^{-1}$, in a fixed bed or fluidized bed or moving bed reactor or a combination thereof. The ratio of alkane to diluent or mixture of diluents varies from 1:0.1 to 1:10. The conversion of light paraffins is achieved in the range of 35-60 wt % with the selectivity for respective light olefin in the range of 40-90 wt %.

In a preferred feature, the catalyst composition obtained by the process disclosed in the present invention shows selectivity for propylene in the range of 40-90 wt %.

The disclosed method of catalyst preparation is not only confined to preparation of catalysts for alkane dehydrogenation process and is applicable to any process which requires porous catalyst and/or high dispersion of metals impregnated on the catalyst. Examples of such processes are catalytic reforming, hydrotreating, etc.

The following are the advantages of the present invention:
1. Novel method for preparation of a catalyst for dehydrogenation of paraffins to light olefins with high selectivity for propylene.
2. Enhancement of catalyst activity and selectivity by the addition of carbonaceous materials during the process of catalyst preparation.

The following examples are given for the purpose of further illustrating the invention. All percentages and parts are based on weight unless otherwise indicated.

Carbonaceous Material Used in Catalyst Preparation

The Petroleum coke used in the following examples was prepared by pulverizing the coke obtained from Delayed coker unit, followed by calcination at 1250° C. (ramp rate of 5° C./min) for 4 hours under nitrogen atmosphere. The metal analysis report of the calcined coke is represented as Table 1.

TABLE 1

Metal analysis report of the calcined Petroleum coke

| Metal | Concentration (ppm) |
|---|---|
| Fe | 283 |
| Mg | 15 |
| Na | 5.4 |
| Ni | 169 |
| V | 78 |
| Si | 102 |

The activated charcoal used in the following examples has Surface area of 926 $m^2/g$ and pore volume of 0.7 cc/g.

Example 1

Preparation of Dehydrogenation Catalyst Using Petroleum Coke or Activated Charcoal To prepare the Dehydrogenation catalyst using calcined petroleum coke, 38.5 g of alumina (on dry basis) and 4.0 g of petroleum coke were taken
  (i) Coke was subjected to wet grinding until particles of size <5 microns were obtained.
  (ii) 120 mL of diluted formic acid (containing 10 vol % HCOOH in distilled water) was taken in a beaker and kept under continuous stirring.
  (iii) Measured amount of alumina was added to the beaker and allowed to mix for 15-20 mins to form a gel. The prepared gel was further aged for 15-20 minutes.
  (iv) Simultaneously, 29.5 g of chromium nitrate nonahydrate (98% purity) and 0.974 g of anhydrous potassium nitrate (99% purity) were dissolved together in 20 mL of DM water.
  (v) The grinded paste of coke obtained from step (i) and the solution from step (iv) were then added to the alumina gel under continuous stirring to make homogenous catalyst slurry (15 mL of water was gradually added to prevent the formation of lumps and maintain the consistency/flow ability).
  (vi) The catalyst slurry was dried in oven at 120° C. for 12-16 hours to get a dry cake of catalyst.
  (vii) The dried cake was crushed and sieved to obtain particles of 0.5-1.0 mm, as suitable for fixed bed operation. Alternatively, the catalyst could be crushed and sieved to get particles of 20-200 microns for fluidized bed operation.
  (viii) The catalyst was then calcined at 600° C. (ramp rate of 2.0° C./min) for 2 hours in presence of air.

Thus, the catalyst prepared utilizing petroleum coke is labeled as Cat-1A, and its physical properties are indicated in Table 2. According to the procedure explained above, the catalyst, Cat-2A was prepared by using activated charcoal instead of petroleum coke, with remaining steps of the procedure being the same. And, the catalyst, Cat-3A was prepared without the addition of coke, by following the procedure elaborated above. The physico-chemical properties of catalysts, Cat-1A and Cat-2A are compared with that of Cat-3A in Table 2. The performance of the catalysts, Cat-1A, Cat-2A and Cat-3A was tested according to the method presented in Example 2.

Cat-1B was prepared by subjecting Cat-1A to reduction in a fixed bed/fixed-fluidized bed reactor using Hydrogen gas, at 600-800° C. at a controlled flow rate. Catalysts, Cat-2B and Cat-3B were prepared in the similar way. The performance of the catalysts, Cat-1B, Cat-2B and Cat-3B was evaluated as per the method presented in Example 3.

TABLE 2

Physico-chemical properties of the catalysts prepared using petroleum coke and activated charcoal

| Catalyst | Amount of carbonaceous material added (wt % of catalyst) | SA ($m^2/g$) | PV (cc/g) | Metal concentration (wt %) | Catalyst composition (wt %) |
|---|---|---|---|---|---|
| Cat-1A | 9 | 216 | 0.242 | Cr: 8.4; K: 0.82 | $Cr_xO_y$: 12.28; $K_2O$: 0.99; $Al_2O_3$: 86.7; Trace amount of Na, Fe, Ni, & V |
| Cat-2A | 9 | 201 | 0.232 | Cr: 8.35; K: 0.81 | $Cr_xO_y$: 12.20; $K_2O$: 0.98; $Al_2O_3$: 86.8; Trace amount of Na |
| Cat-3A | 0 | 196 | 0.234 | Cr: 8.6; K: 0.8 | $Cr_xO_y$: 12.57; $K_2O$: 0.96; $Al_2O_3$: 86.4; Trace amount of Na |

Example 2

Performance Evaluation of Catalysts for Oxidative Propane Dehydrogenation Process The performance of the catalysts, Cat-1A, Cat-2A and Cat-3A, was evaluated using a fixed-bed tubular reactor of 9 mm ID containing 1-2 g catalyst at reaction temperature of 630-700° C., as measured by the thermocouple located in the catalyst bed. The feed stream contained propane, $CO_2$ and $N_2$ in the molar ratio of C3:CO2:N2=26:53:21 and Gas hourly space velocity (GHSV) of the feed gas was 800-2000 $h^{-1}$. The flow rates of inlet gases were controlled by mass flow controllers. The inlet and outlet gas compositions were analyzed in a Refinery Gas Analyzer equipped with TCD and FID at regular intervals. Propane conversion, propylene yield and selectivity were calculated using the following formulae, and the propylene selectivity achieved in each case is indicated in Table-3. The data shown in Table-3 is calculated based on the product composition at 20 minutes after the start of the run.

$$\% \text{ Conversion} = \frac{\text{weight of propane (in)} - \text{weight of propane (out)}}{\text{weight of propane (in)}} * 100$$

$$\% \text{ Yield} = \frac{\text{weight of propylene formed}}{\text{weight of propane (in)}} * 100$$

$$\% \text{ Selectivity} = \frac{\text{Propylene yield}}{\text{Propane conversion}} * 100$$

TABLE 3

Propylene selectivity achieved using catalysts prepared for Oxidative PDH process using $CO_2$

| Catalyst | Propylene selectivity (wt %) | Ratio of propylene to ethylene yields |
|---|---|---|
| Cat-1A | 46 | 3.7 |
| Cat-2A | 49.1 | 5.2 |
| Cat-3A | 44.4 | 3.5 |

Example 3

Performance Evaluation of Catalysts for Non-Oxidative Propane Dehydrogenation Process The performance of the catalysts, Cat-1B, Cat-2B and Cat-3B, was evaluated using a fixed-bed tubular reactor of 9 mm ID containing 1-2 g catalyst at reaction temperature of 600-650° C., as measured by the thermocouple located in the catalyst bed. The feed stream contained propane and $N_2$ in the molar ratio of $C_3:N_2=1:2$ and Gas hourly space velocity (GHSV) of the feed gas was 1000-3500 $h^{-1}$. The flow rates of inlet gases were controlled by mass flow controllers. The inlet and outlet gas compositions were analyzed in a Refinery Gas Analyzer equipped with TCD and FID at regular intervals. Propane conversion, propylene yield and selectivity were calculated using the formulae as given in example 2, and the obtained results are summarized in Table 4. The data represented in Table-4 is calculated based on the product composition at 20 minutes after the start of the run.

TABLE 4

Propylene selectivity achieved using catalysts prepared for non-oxidative PDH process

| Catalyst | Propylene selectivity (wt %) | Ratio of propylene to ethylene yields |
|---|---|---|
| Cat-1B | 87.1 | 80.2 |
| Cat-2B | 87.5 | 91.0 |
| Cat-3B | 85.8 | 78.5 |

The objective of the present invention is to improve the activity and selectivity of the dehydrogenation catalyst by addition of carbonaceous materials during the preparation and their combustion during calcination subsequently. From examples 2 and 3, it is evident that by employing the method of catalyst preparation disclosed in the present invention, the selectivity of propylene increased from 44.4 wt % to 49.1 wt % for oxidative Propane Dehydrogenation process using $CO_2$ (OPDH) and it increased from 85.8 wt % to 87.5 wt % in case of non-oxidative Propane Dehydrogenation process (PDH). The ratio of propylene yield to ethylene yield in the products improved from 3.5 to 5.2 in case of OPDH and increased from 78.5 to 91.0 in case of PDH, suggesting that the formation of cracking products is greatly suppressed by the disclosed invention process. The selectivity of the products is majorly controlled by the catalyst design/formulation whereas the reactant conversion is mainly a process factor. Therefore, it is important to enhance the desired product selectivity by catalyst design.

The invention claimed is:
1. A process for preparation of a catalyst for dehydrogenation of alkane, wherein the process comprises:
   (a) wet grinding of carbonaceous material to obtain a grinded paste of the carbonaceous material;
   (b) adding alumina to an organic acid solution under stirring for 15-20 minutes to form alumina gel and ageing the gel for 15-20 minutes;
   (c) preparing aqueous solution of salts of metals of Groups IA and/or VIB and/or VIII using suitable metal salts;
   (d) adding the grinded paste of the carbonaceous material obtained in step (a) and the aqueous solution of salts of metals obtained in step (c) to the alumina gel obtained in step (b) to obtain a homogeneous catalyst slurry;
   (e) drying the catalyst slurry obtained in step (d) at 100-150° C. for 12-16 hours to get a dry cake of catalyst;
   (f) crushing the dry cake of catalyst obtained in step (e) and sieving to obtain catalyst particles of 0.5-1.0 mm for fixed bed operation and particles of 20-200µ for fluidized bed operation;
   (g) calcining the catalyst particles obtained in step (f) at 600-650° C. at a ramp rate of 2.0° C./min for 2 hours in presence of air; and
   (h) reducing the catalyst obtained in step (g) in a fixed bed/fixed-fluidized bed reactor using hydrogen gas, at 600-800° C. at a controlled flow rate to obtain final catalyst.

2. The process as claimed in claim 1, wherein the carbonaceous material is selected from the group comprising of petroleum coke, activated charcoal, graphite powder, and a combination thereof.

3. The process as claimed in claim 1, wherein in step (a) the carbonaceous material is grinded to a particle size ranging from 1 to 5µ.

4. The process as claimed in claim 1, wherein in step (b) the organic acid is formic acid.

5. The process as claimed in claim 1, wherein in step (b) the organic acid solution is prepared by adding 10% by volume of formic acid in distilled water.

6. The process as claimed in claim 1, wherein the metal of Group VIB is selected from group consisting of chromium, molybdenum, and tungsten.

7. The process as claimed in claim 1, wherein the metal of Group VIII is selected from group consisting of iron, cobalt, rhodium, iridium, nickel, palladium, and platinum, and the metal of Group IA is selected from group consisting of lithium, sodium, potassium, rubidium, and cesium.

* * * * *